United States Patent
Karavas et al.

(10) Patent No.: US 11,318,114 B2
(45) Date of Patent: May 3, 2022

(54) WATER DISPERSIBLE MINI-TABLETS COMPRISING ENALAPRIL FOR TREATMENT OF HYPERTENSION IN A PEDIATRIC POPULATION AND METHOD OF PREPARATION THEREOF

(71) Applicant: PHARMATHEN S.A., Pallini-Attikis (GR)

(72) Inventors: Evangelos Karavas, Pallini Attikis (GR); Efthymios Koutris, Pallini Attikis (GR); Vasiliki Samara, Pallini Attikis (GR); Ioanna Koutri, Pallini Attikis (GR); Anastasia Kalaskani, Pallini Attikis (GR); Lida Kalantzi, Pallini Attikis (GR); Andreas Kakouris, Pallini Attikis (GR); Amalia Diakidou, Pallini Attikis (GR); George Gotzamanis, Pallini Attikis (GR); Zaharias Georgousis, Pallini Attikis (GR); Louiza Konstanti, Pallini Attikis (GR)

(73) Assignee: PHARMATHEN S.A., Pallini-Attikis (GR)

( * ) Notice: Subject to any disclaimer, the term of this patent is extended or adjusted under 35 U.S.C. 154(b) by 545 days.

(21) Appl. No.: 15/326,767

(22) PCT Filed: Jun. 19, 2015

(86) PCT No.: PCT/EP2015/001242
§ 371 (c)(1),
(2) Date: Jan. 17, 2017

(87) PCT Pub. No.: WO2016/015797
PCT Pub. Date: Feb. 4, 2016

(65) Prior Publication Data
US 2017/0202804 A1    Jul. 20, 2017

(30) Foreign Application Priority Data

Jul. 31, 2014  (WO) ................. PCT/EP2014/002096

(51) Int. Cl.
| | | |
|---|---|---|
| *A61K 9/20* | (2006.01) | |
| *A61K 31/401* | (2006.01) | |
| *A61K 9/00* | (2006.01) | |
| *B65B 1/00* | (2006.01) | |
| *B65B 63/02* | (2006.01) | |

(52) U.S. Cl.
CPC .......... *A61K 31/401* (2013.01); *A61K 9/0095* (2013.01); *A61K 9/2009* (2013.01); *A61K 9/2013* (2013.01); *A61K 9/2018* (2013.01); *A61K 9/2027* (2013.01); *A61K 9/2095* (2013.01); *B65B 1/00* (2013.01); *B65B 63/02* (2013.01)

(58) Field of Classification Search
CPC .. A61K 9/0095; A61K 9/2009; A61K 9/2013; A61K 9/2018; A61K 9/2027; A61K 9/2095; A61K 31/401; B65B 1/00; B65B 63/02
See application file for complete search history.

(56) References Cited

U.S. PATENT DOCUMENTS

| 5,562,921 A | 10/1996 | Sherman |
| 8,778,366 B2 | 7/2014 | Rajewski |

FOREIGN PATENT DOCUMENTS

| EP | 1944017 A2 | 7/2008 |
| WO | WO/1998/26765 A1 | 6/1998 |

OTHER PUBLICATIONS

Patel et al. Pharmagene. 2013; 1(2): 10-21.*
Thomson et al. Pediatrics. 2009; 123(2): abstract.*
Momma. Paediatr Drugs. 2006; 8(1): abstract.*
Uzunovic et al. Bosnian Journal of Basic Meedical Sciences. 2007; 7(3): 279-283.*
Written Opinion of the ISR, WIPO, PCT/EP2015/001242.
Al-Omari M.M. et al.: "Effect of the Drug-Matrix on the Stability of Enalapril Maleate in Tablet Formulations", Journal of Pharmaceutical and Biomedical Analysis, New York, NY, US, vol. 25, No. 5-6, (Jul. 2001) pp. 893-902.
Wells Thomas et al.:, "A Double-Blind, Placebo-Controlled Dose-Response Study of the Effectiveness and Safety of Enalapril for Children With Hypertension", Journal of Clinical Pharmacology, Aug. 2002, vol. 42, No. 8, pp. 870-880.

* cited by examiner

*Primary Examiner* — David Browe
(74) *Attorney, Agent, or Firm* — AKC Patents, LLC; Aliki K. Collins

(57) ABSTRACT

The present invention relates to water dispersible mini-tablets of Enalapril or a pharmaceutically acceptable salt thereof for use in the treatment of hypertension in a pediatric population. The pediatric population is defined as 0 to 18 years of age. The water dispersible mini-tablets of Enalapril further include a disintegrant, a diluent, a lubricant and a glidant. The active ingredient is distributed evenly in the mini-tablet and the disintegrant comprises Crospovidone. The mini-tablet has a diameter of 3 mm and disintegrates in less than 15 seconds in water.

10 Claims, No Drawings

WATER DISPERSIBLE MINI-TABLETS COMPRISING ENALAPRIL FOR TREATMENT OF HYPERTENSION IN A PEDIATRIC POPULATION AND METHOD OF PREPARATION THEREOF

TECHNICAL FIELD OF THE INVENTION

The present invention relates to water dispersible mini-tablets of Enalapril or a pharmaceutically acceptable salt thereof for use in the treatment of hypertension in a pediatric formulation. The pediatric population is defined as 0 to 18 years of age. The present invention also provides a method of manufacturing of such dosage form.

BACKGROUND OF THE INVENTION

Hypertension or high blood pressure is a serious health issue in many countries. Blood pressure is the product of cardiac output and peripheral vascular resistance and is created by the force exerted by the circulating blood on the walls of the blood vessels. The higher the blood pressure the harder the heart needs to work. Statistics show that 1 in 3 adults in developed countries have hypertension. If left untreated, it is considered a substantial risk factor for cardiovascular and other diseases including coronary heart disease, myocardial infarction, congestive heart failure, stroke and kidney failure. Hypertension is classified as primary or essential hypertension and secondary hypertension. Primary hypertension has no known cause and may be related to a number of environmental, lifestyle and genetic factors such as stress, obesity, smoking, inactivity and sodium intake. Secondary hypertension can be caused by drug or surgical interventions, or by abnormalities in renal, cardiovascular or the endocrine system.

In adults, hypertension is defined regardless of age, sex or body weight as blood pressure being 140/90 mm Hg or higher in stage 1 hypertension and 160/100 mm Hg or higher in stage 2 hypertension. In children, hypertension is characterized as blood pressure being between the $95^{th}$ and $99^{th}$ percentile (of the child's age, sex and height) plus 5 mm Hg in stage 1 and blood pressure above the $99^{th}$ percentile (of the child's age, sex and height) plus 5 mm Hg is characterized as stage 2 hypertension. If stage 1 is asymptomatic and without organ damage it allows time for evaluation before initiation of treatment; whereas in stage 2 prompt evaluation and treatment are required.

Hypertension in now more commonly observed in children and adolescents with a 2-9% incidence depending on age, sex and ethnicity and is associated with long term risks of ill-health. The prevalence of hypertension in children is increasing due to the rise in obesity in children. Symptoms include headache, fatigue, blurred vision, epistaxis, Bell's palsy and sleep-disordered breathing. Hypertension in children and adolescents is treated with lifestyle changes, including weight loss, a healthy, low-sodium diet, regular physical activity and avoidance of tobacco and alcohol. However, in children with symptomatic hypertension, secondary hypertension, target organ damage, diabetes or persistent hypertension should be treated with antihypertensive medications promptly. In addition, a child with blood pressure greater than or equal to $95^{th}$ percentile in a medical setting but normal pressure outside the office is said to have white coat hypertension.

In neonates hypertension is discovered on routine monitoring of vital signs. The blood pressure in infants in influenced by various factors, including birth weight, gestational age, and postconceptual age. Other presentations of neonatal hypertension to be aware of in acutely ill infants include congestive heart failure and cardiogenic shock, which are potentially life threatening but can gradually resolve with appropriate blood pressure reduction. Symptoms in infants include feeding difficulties, unexplained tachypnea, apnea, lethargy, irritability or seizures and in older infants unexplained irritability or failure to thrive may be the only manifestations.

The causes of hypertension in children and adolescents are similar to those in adults. Nevertheless, most common etiologies in children are observed in younger children rather than adolescents and in particular those with stage 2 hypertension. The younger the age of the child the higher the probability is of identifying the underline cause of stage 2 hypertension. In children under 12 years of age, renal disease and renovascular hypertension are the most common causes, followed by aortic coarctation and primary hypertension. Endocrine causes such as pheochromocytoma, primary aldosteronism and Cushing's syndrome are more rare causes. In children over 12 years of age, primary hypertension is the most common cause and is characterized by elevated systolic blood pressure or elevated systolic and diastolic blood pressure. More recently, obstructive sleep apnea has been recognized as a cause of secondary hypertension; the condition being more prevalent in obese children and adolescents.

A number of antihypertensive drugs are available for treating hypertension. The various therapeutic classes included alpha-adrenergic blockers, beta-blockers, calcium channel blockers, hypotensives, mineralcorticoid antagonists, central alpha-agonists, diuretics, and renin-angiotensin-aldosterone inhibitors which include angiotensin II receptor antagonists and angiotensin-converting enzyme inhibitors (ACE).

ACE inhibitors in particular, inhibit the angiotensin-converting enzyme which is a peptydyl dipeptidase that catalyzes angiotensin I to angiotensin II, a potent vasoconstrictor involved in regulation of blood pressure. However, the treatment of hypertension in children has proven more difficult since there are no anti-hypertensive dosage forms available, that are suitable for administration to children. Since the dosage required to treat hypertension in children is much smaller, the parent needs to use the adult drug dosage form and cut it keeping in mind the weight of the child. This can lead to miscalculations of the required dose and more importantly it can result in the parent not giving a stable dose to the child resulting in inadequate treatment. Furthermore, tablets and capsules are harder to administer to children of a younger age without causing complaining and/or emesis and therefore treatment compliance might be difficult.

Enalapril is a prodrug belonging to the ACE inhibitor medications. It is rapidly hydrolyzed in the liver to Enalaprilat following oral administration and is excreted primarily by renal excretion. In addition to treating hypertension, Enalapril has been used for treatment of symptomatic heart failure and assyptomatic left ventricular dysfunction. Its chemical name is (2S)-1-{[92S0-1-ethoxy-1-oxo-4phenylbutan-2-yl]amino}pyrrolidine-2carboxylic acid and it has a molecular weight of 376.447 g/mol. U.S. Pat. Nos. 4,374,829, 4,374,829, 4,472,380 and 4,510,083 disclose Enalapril and methods for its preparation.

Enalapril has been marketed as a tablet in its maleate salt form, however there is no available children's dosage form in the market. Enalapril maleate has a molecular weight of 492.5, it is an off-white polymorphic crystalline powder and is freely soluble in methanol and dimethylformamide, soluble in alcohol, sparingly soluble in water, slightly soluble in semi polar organic solvents and practically insoluble in nonpolar organic solvents. Enalapril maleate is a derivative of two amino acids: L-alanine and L-proline. The maleate salt of Enalapril differs structurally from Enalaprilat by the presence of an ethoxycarbonyl group rather than a carboxy group at position 1 of L-alanyl-L-proline and the presence of the maleate salt. These structural modifications result in increased absorption of Enalapril maleate at the gastrointestinal tract (GI) compared to Enalaprilat.

It is known in the art that many compounds that inhibit ACE have poor stability either in the form of free acids or salts, when they are in a pharmaceutical dosage form. These compounds easily decompose, first of all by hydrolysis and intramolecular cyclization, but the amount of other decomposition products is often not identified. This is particularly true for Enalapril and its maleate salt and it becomes clear from the prior art.

According to EP0545194 Enalapril sodium salt is more stable in pharmaceutical dosage forms than Enalapril maleate salt. Furthermore, EP0264887 suggest the use of ascorbic acid as an antioxidant or color stabilizing agent when the API is an ACE inhibitor.

In addition, U.S. Pat. No. 5,562,921 discloses that Enalapril degrades at a faster rate in the presence of some diluents namely microcrystalline cellulose, dibasic calcium phosphate, and tribasic calcium phosphate, lubricants, namely magnesium stearate and calcium stearate, and disintegrants such as crospovidone, and sodium starch glycolate. The composition disclosed was free of microcrystalline cellulose, cellulose derivatives or cellulose polymers, calcium phosphate, disintegrants, and magnesium stearate. At least 50% by weight of the pharmaceutical excipients in the composition were pharmaceutically acceptable water soluble substances such that the composition could dissolve sufficiently rapidly and not require disintegrants. Moreover, U.S. Pat. No. 4,743,450 discloses the use of stabilizers to minimize the cyclization, hydrolysis and coloration of ACE inhibitors.

Dispersible tablets are solid, orally administered pharmaceutical forms which must dissolve evenly in less than one minute in water. The parameters defining dispersible tablets are their high speed of disintegration in water and the uniformity of dispersion of the particles into which they disintegrate. Both the disintegration rate and the dispersion uniformity depend on the pharmaceutically acceptable excipients and the active ingredient. A dispersible tablet that is diluted in water can potentially be administered to a pediatric population of all ages, even in the age group of 0 to 1 year. There is no known marketed dispersible tablet, such as a dispersible minitablet, comprising Enalapril that is suitable for the treatment of hypertension in a pediatric population.

There still remains a need to manufacture a dosage form for the treatment of hypertension in a pediatric population from 0 to 18 years of age that is easy to swallow, it has no risk of choking and/or aspiration, it has a pleasant taste and therefore it has increased compliance compared to other dosage forms targeting adult populations and is has an easy and cost effective manufacturing process. There still remains a need for an effective and safe anti-hypertensive treatment in children meeting all the above criteria and the objective of the present invention is to provide such a dosage form.

SUMMARY OF THE INVENTION

The main objective of the present invention is to develop a water dispersible minitablet comprising an anti-hypertension medication such as Enalapril or a pharmaceutically acceptable salt thereof. The dispersible minitablet of the present invention is suitable for administration to a pediatric population of a specific age group.

It is, therefore, an object of the present invention to provide a thermodynamically stable and efficient product in the form of a dispersible minitablet with a reduced amount of impurities but without reduced half-life; comprising Enalapril or a pharmaceutically acceptable salt thereof for the treatment of hypertension in children.

An object of the present invention is to manufacture water dispersible minitablets comprising Enalapril or a pharmaceutically acceptable salt thereof that is suitable for administration to a pediatric population of 0 to 18 years of age, but is particularly safe for administration to infants from 0 to 1 year. Another aspect of the present invention is that the palatability of the solution formed is well received from the pediatric population, even though a minimum amount of a sweetener is added.

Another object of the present invention is to provide a water dispersible minitablet of a single strength and 3 mm in diameter comprising Enalapril or pharmaceutically acceptable salts thereof, wherein the strength of the dosage administered can be easily adjusted according to the age and the weight of the pediatric population; therefore the present invention has a particularly small cost of manufacturing.

An object of the present invention to provide a water dispersible minitablet formulation comprising Enalapril or pharmaceutically acceptable salts thereof together with a disintegrant, a diluent, a glidant, a lubricant and any other suitable pharmaceutical excipient or combinations thereof; wherein the manufacturing technique is simple and cost effective.

A further object of the present invention is to provide a manufacturing process for the preparation of the minitablets comprising the following steps:
Weighing of raw materials
Mixing the pharmaceutically acceptable excipients and API until a homogenous powder is formed
Lubricating the mixture
Compacting the mixture into minitablets by direct compression
Packaging of the minitablets individually in aluminum-aluminum blister foils (Alu-Alu blister packs)

Other objects and advantages of the present invention will become apparent to those skilled in the art in view of the following detailed description.

DETAILED DESCRIPTION OF THE INVENTION

The main object for the present invention is to provide a minitablet formulation that can be dispersed in water to form a solution which can be administered to a pediatric population of a specific age for the treatment of hypertension, comprising Enalapril or pharmaceutically acceptable salts thereof.

For the purpose of the present invention, a pharmaceutical composition comprising an active agent or a combination of active agents is considered "stable" if said agent or combination of agents degrades less of more slowly than it does on its own or in known pharmaceutical compositions.

The manufacturing of dispersible tablets and minitablets requires taking into consideration the physicochemical incompatibilities of the active ingredient and searching of suitable pharmaceutically acceptable excipients enabling the requirement of various Pharmacopeas to be fulfilled.

The parameters to be considered when using direct compression for the manufacturing of dispersible tablets and minitablets are their high speed of disintegration in water and the uniformity of dispersion of the particles into which they disintegrate. Disintegration rate and dispersion uniformity depend on the combination of the API with the excipients. Thus disintegration as a measure of the release of the active ingredient of the compressed pharmaceutical preparations is the critical parameter in the development of the dispersible forms, so that the selection of the excipients is the most important phase.

The pharmaceutical formulation of the present invention is suitable for the manufacturing of a water dispersible minitablet comprising Enalapril or a pharmaceutically acceptable salt thereof and can further comprise suitable quantities of disintegrants, lubricants, glidants, and optionally sweeteners and flavorings.

Because the most critical parameter in the water dispersible minitablet is the rate of disintegration, the selection of the appropriate disintegrant is one of the most important steps in the manufacturing process. In the sense used in the description the term "disintegrant" refers to an agent which creates an increase in the surface so that the API of the tablet is released very quickly. Suitable disintegrants include, but are not limited to, sodium starch glycolate, polymeric derivatives of acrylic acid and crospovidone. Crospovidone is the preferred disintegrant of the present invention. It is also known as insoluble polyvynivylpyrrolidone (PVP) and is obtained by polymerization of vinylpyrrolidone. It is believed that the high disintegrating action of the reticulated and insoluble Crospovidone is due to its very high hydration capacity which means that a very high disintegration rate is attained with the resulting enhancement of the dissolution of Enalapril in water. The concentration of Crospovidone in the formulation can be from 3 to 14% w/w, preferably from 4 to 7% w/w and more preferably from 5 to 6% w/w of the total weight of the formulation.

The selection of the direct compression technique for the manufacturing of the dispersible minitablets of the present invention has a further advantage in the choice of excipients. The possibility of using the disintegrant in extragranular form enhances its swelling effect, since the disintegration effect is not altered either by humectation or by drying.

Diluents include excipients that facilitate compression of powdery materials and give the tablet its strength. Diluents can be selected from, but are not limited to, the group consisting of microcrystalline cellulose (MCC), lactose, mannitol such as Pearlitol®, hydroxypropyl cellulose (HPC), low substituted HPC, pregelatinized starch, dry flowing starch, sucrose, glucose, sorbitol and combinations thereof. The preferred diluent of the present invention is Pearlitol® because it enables tablets to be manufactured with a high degree of purity using the direct compression technique. The concentration of Pearlitol® is from 55 to 95% w/w, preferably from 80 to 97% w/w and more preferably from 85 to 90% w/w of the total weight of the formulation.

Lubricants include excipients with reduced inter-particle friction inside the tablet, reducing the reaction forces appearing on the walls of the matrix. The addition of the lubricant enhances the slipping of the formulation to be compressed. It also ensures even filling of the space in the matrix so that there is very little or no tablet weight variation. Lubricants suitable for use in the present invention include, but are not limited to, talc, stearyl sodium fumarate, magnesium stearate, silica, stearin, stearic acid or combinations thereof. The preferred lubricant of the present invention is magnesium stearate in a concentration of from 0.1 to 1.0% w/w, preferably from 0.2 to 0.7% w/w, more preferably from 0.4 to 0.6% w/w of the total weight of the formulation.

Glidants can be used in combination with lubricants to prevent particle adhesion, so avoiding or reducing compacting and limiting friction between them. The glidant can also act as an absorbent, capturing the humidity which would be taken up by Enalapril, so slowing the degradation of the active ingredient by hydrolysis. Glidants used can be selected from, but are not limited to, the group consisting of colloidal silicon dioxide, talc, calcium phosphate dibasic, calcium phosphate tribasic and combinations thereof. The preferred glidant of the present invention is talc and is incorporated in the formulation in a concentration from 0.1 to 8% w/w, preferably from 2 to 6% w/w and more preferably from 2 to 4% w/w of the total weight of the formulation.

The formulation of the present invention may also comprise sweeteners and flavorings. Sweeteners for a more pleasant taste can be selected from the group consisting of sucrose, glucose, maltose, sucralose, oligosaccharides dextrin, alpha cyclodextrin, beta cyclodextrin, gamma cyclodextrin, methyle beta cyclodextrin, cluster dextrin, invert sugar, fructose, lactose, galactose, starch syrup, sorbitol, maltilol, xylitol, erythritol, hydrogenated starch syrup, mannitol, trehalose, saccharin and combinations thereof. The amount of the sweetener can range from 0.4 to 5% w/w of the total weight of the formulation.

Flavoring agents can be used to improve the taste of the formulation such as a natural flavor, an artificial flavor or a mixture thereof. The natural flavor may include aromatic plants, especially extracts and/oils obtained from leaves, flowers or fruits of such plants and can include spearmint oil, cinnamon oil, peppermint oil, lemon, oil, clove oil, bay oil, thyme oil, nutmeg oil, sage oil, almond oil and the like. The artificial flavoring may include synthetic fruit flavors such as lemon, orange, grape, lime, strawberry, etc and other synthetic flavors such as vanilla, chocolate, coffee, cocoa, ginseng, citrus etc. The amount of the flavoring agent can range from 1 to 15% by weight of the total weight of the formulation. Surprisingly, the addition of a sweeteners or a flavoring was not required for the formulation of the present invention, making the formulation even more suitable for administration to a pediatric formulation.

Dispersible tablets are very sensitive to damp and their stability is compromised by granulation operations, therefore direct compression is the preferred technique as the one with the most advantages. On one hand, manufacture is rapid and on the other is avoids possible degradation of the active ingredient. The risk of contamination is also reduced. However, the most significant advantage is that directly compressed tablets normally disintegrate more rapidly than those made by wet granulation, which require the addition of agglutinant agents, which slow the disintegration rate.

While direct compression may cause some drawbacks, such as problems of uniformity of the tablet and compressibility of the tablet, surprisingly none of these problems arose. In fact, the tablets varied very little in weight and content of the active ingredient. Compressibility was acceptable and tablet hardness and disintegration rate were within the required limits.

Dispersible minitablets comprising Enalapril may be manufactured by a standard process, for example in a conventional rotary or eccentric compressing machine which compresses the prepared pharmaceutical fed to the machine. The dispersible minitablet prepared according to the present invention is solid, intended for oral use, of uniform appearance, and with sufficient mechanical strength to bear possible damage from storage and transport with hardness strength from 19 to 32 N. The active ingredient is distributed evenly in the pharmaceutical form and the disintegration rate is surprisingly very high with a disintegration time of less than 1 minute, preferably less than 30 seconds, more preferably less than 15 seconds and most preferably the disintegration time is from 4 to 6 seconds. The minitablets of the present invention will have a size of 3 mm diameter, another factor contributing to the very fast disintegration rate. Finally the taste of the solution when the minitablets are dispersed in water is neutral as there is no addition of a sweetener or a flavoring making it suitable for administration to a pediatric population without the risk of addiction to sugar and it is also suitable for administration to diabetic patients.

To measure the disintegration time of the minitablets the standard *Pharmacopoeia* (*Ph. Eur.* 01/2009:20901) test and disintegration machine were used. However, because of the very small size of the minitablet an additional method was used using a rotor as the disintegration vessel. In particular, 5 minitablets and 5 ml water were placed in a 10 ml vial, which was then placed in a rotor with a speed of 36 rpm and the disintegration time was measured. Disintegration times of less than 1 minute are considered as "fast disintegration".

The process according to the present invention for the manufacturing of dispersible minitablets comprising Enalapril or acceptable salts thereof comprises of the following steps:

Weighing of raw materials
Mixing the pharmaceutically acceptable disintegrant, diluent and glidant with the API until a homogenous powder is formed
Lubricating the mixture with the addition of a lubricant
Compacting the mixture into minitablets by direct compression
Packaging of the minitablets individually in aluminum-aluminum blister foils (Alu-Alu blister packs)

The preferred form of Enalapril is Enalapril maleate. Surprisingly, the water dispersible minitablets of the present invention are stable and Enalapril maleate impurities were kept to a minimum. Another significant advantage of the present invention is that the desired concentration of the minitablet is established as 0.3125 mg per tablet. Since the concentration administered to a pediatric population for any medication is determined according to the age group and the weight of the child; the present invention has an additional advantage. Depending on the child's weight an appropriate number of minitablets can be dispersed in an appropriate amount of water. This also minimizes the manufacturing cost of the present invention.

For a dosing strength from 0.08 to 0.50 mg/Kg depending on the child's weight the following conditions have been developed. For children weighing≥4 Kg 1 minitablet (0.3125 mg) can be dispersed in 2 ml of water. For children weighing<4 Kg and ≥6 Kg 2 minitablets (0.625 mg) can be dispersed in 2 ml of water. For children weighing<6 Kg and ≥9 Kg 3 minitablets (0.9375 mg) can be dispersed in 2 ml of water. For children weighing<9 Kg and ≥12 Kg 4 minitablets (1.25 mg) can be dispersed in 2 ml of water. For children weighing<12 Kg and ≥18 Kg 6 minitablets (1.875 mg) can be dispersed in 2 ml of water. This dosing is possible because Enalapril is soluble in water with a solubility of 25 mg/ml. More preferably the dosing is from 0.08 mg/Kg to 0.31 mg/Kg once daily.

In cases where the physician prescribes a starting dose lower than 0.8 mg/Kg the following procedure can be followed. 2 minitablets (0.625 mg) can be diluted in 4 ml of water for a final concentration of 0.16 mg/ml. A fraction of the solution can be administered corresponding to the appropriate dose depending on the child's weight. In addition in cases where the starting dose is much higher the dose can even be as high as 1.65 mg/ml if 18 minitablets are dispersed in 5 ml of water.

A reusable dispenser and a 5 ml dosing device as well as complete instructions according to the dosage strength required will be provided in the package along with storage instructions making the administration of the dosage easy for all parents/caregivers. Another advantage of the present invention is that the risk of overdose or dosing errors is diminished.

The present invention will be described in greater detail by the following examples. However, these examples are intended for illustrative purposes and it will be appreciated by a person skilled in the art that these examples do not restrict the scope of the present invention in any way.

EXAMPLES

Example 1

A number of different disintegrants and diluents were used in various combinations in an experimental design to identify the best suitable pharmaceutically acceptable excipients for the water dispersible minitablet formulation comprising Enalapril maleate. Excipients included Ac-Di-Sol®, Crospovidone, Primojel®, low-substituted HPC, sucralose, Pearlitol®. It was established that the best physicochemical characteristics for the minitablets were acquired with the formulation comprising Crospovidone and Pearlitol®. The following formulation was developed shown in Table 1 and the physicochemical characteristics including hardness and disintegration time with two different techniques as described in the description were measured from 3 experiments shown in Table 2.

TABLE 1

| Formulation of Trial 1 | | |
| --- | --- | --- |
| TRIAL 1 | % | Mg/minitab |
| Enalapril maleate | 1.805 | 0.3125 |
| Crospovidone | 11.552 | 2 |
| Pearlitol ® | 57.762 | 10 |
| Talc | 17.329 | 3 |
| Magnesium Stearate | 11.552 | 2 |
| Total (mg) | 100.000 | 17.313 |

TABLE 2

Physicochemical characteristics of Trial 1 measured in a disintegration machine and a rotor.
Results are shown from 3 different experiments.

| Hardness (N) | Disintegration Machine (sec) | Rotor (sec) |
| --- | --- | --- |
| 16 | 31 | 50 |
| 16 | 31 | 57 |
| 16 | 34 | 47 |

Example 2

In order to improve the disintegration of the formulation of Trial 1 the amounts of the lubricant and the glidant were reduced and the following two formulations were developed shown in Table 3. The physicochemical characteristics of the Trials of example 2 were measured in three different experiments and are shown in Table 4.

TABLE 3

Formulations of example 2

|  | Trial 2 (%) | Trial 2 (Mg/minitab) | Trial 3 (%) | Trial 3 (Mg/minitab) |
|---|---|---|---|---|
| Enalapril maleate | 2.262 | 0.3125 | 2.330 | 0.3125 |
| Crospovidone | 14.480 | 2 | 14.911 | 2 |
| Pearlitol ® | 72.398 | 10 | 74.557 | 10 |
| Talc | 7.240 | 1 | 7.456 | 1 |
| Magnesium Stearate | 3.620 | 0.5 | 0.746 | 0.1 |
| Total (mg) | 100.000 | 13.81 | 100.00 | 13.41 |

TABLE 4

Physicochemical characteristics of Trial 2 and Trial 3 measured in a disintegration machine and a rotor. Results are shown from 3 different experiments.

| Trial 2 | | | Trial 3 | | |
|---|---|---|---|---|---|
| Hardness (N) | Disintegration Machine (sec) | Rotor (sec) | Hardness (N) | Disintegration Machine (sec) | Rotor (sec) |
| 24 | 8 | 16 | 16 | 3 | 6 |
| 23 | 9 | 18 | 20 | 5 | 7 |
| 19 | 6 | 13 | 14 | 5 | 4 |

Example 3

To further improve the friability of the minitablet it was necessary to increase the hardness values. In addition the disintegration time needed optimization. In the next trial the amount of Pearlitol® was increased and the amount of Crospovidone and Talc were decreased. Trial 4 is shown in Table 5 and the physicochemical characteristics of three experiments are shown in Table 6.

TABLE 5

Formulations of example 3

| Trial 4 | % | Mg/minitab |
|---|---|---|
| Enalapril maleate | 1.848 | 0.3125 |
| Crospovidone | 5.913 | 1 |
| Pearlitol ® | 88.692 | 15 |
| Talc | 2.956 | 0.5 |
| Magnesium Stearate | 0.591 | 0.1 |
| Total (mg) | 100.000 | 16.91 |

TABLE 6

Physicochemical characteristics of Trial 4 measured in a disintegration machine and a rotor. Results are shown from 3 different experiments.

| Hardness (N) | Disintegration Machine (sec) | Rotor (sec) |
|---|---|---|
| 32 | 5 | 6 |
| 29 | 4 | 5 |
| 19 | 5 | 6 |

The formulation of Trial 4 showed really good physicochemical characteristics. The formulation was also tested for taste. The results for taste showed that the taste is neutral. This is a clear advantage because the use of sweeteners and flavorings has been avoided making it a formulation suitable for administration in children of all ages without the risk of addiction to sugar and artificial sweeteners as well as diabetic subpopulations.

The formulation of Trial 4 showed good physicochemical characteristics and a large scale production (5000 minitablets) of the formulation was produced and packaged in Aluminum-Aluminum Blisters packs and subjected to stability tests under various conditions. The results are shown in Table 7.

TABLE 7

Stability studies of Trial 4 in various conditions.

| | Total impurities (%) | | |
|---|---|---|---|
| Time = 0 | 0.42 | | |
| | 25° C. 60% RH | 30° C. 65% RH | 30° C. 75% RH |
| Time = 1 month | 0.57 | 0.81 | 0.96 |
| Time = 6 months | 1.30 | 2.97 | 2.40 |

The invention claimed is:

1. A water-dispersible minitablet comprising:
    Enalapril or pharmaceutically acceptable salts thereof as an active ingredient, a disintegrant, a diluent, a lubricant and a glidant;
    wherein the active ingredient is distributed evenly in the minitablet;
    wherein the minitablet has a diameter of 3 mm;
    wherein the disintegrant comprises Crospovidone; and
    wherein the minitablet disintegrates in less than 15 seconds in water.

2. The water-dispersible minitablet according to claim 1, wherein the diluent is Mannitol, the lubricant is Magnesium stearate and the glidant is Talc.

3. The water-dispersible minitablet according to claim 2, wherein the concentration of Crospovidone is from 5 to 6% w/w of the total weight of the formulation, the concentration of Mannitol is from 85 to 90% w/w of the total weight of the formulation, the concentration of Magnesium stearate is from 0.4 to 0.6% w/w of the total weight of the formulation and the concentration of Talc is from 2 to 4% w/w of the total weight of the formulation.

4. The water-dispersible minitablet according to claim 1, wherein Enalapril is Enalapril maleate salt.

5. The water-dispersible minitablet according to claim 1, further comprising a sweetener, and a flavoring.

6. The water-dispersible minitablet according to claim 1, wherein the minitablet comprises 0.3125 mg of Enalapril per tablet.

7. The water-dispersible minitablet according to claim 1, wherein the minitablet is used for treating hypertension in a pediatric population from 0 to 18 years of age.

8. A method of treating hypertension in a pediatric population comprising administering the minitablet formulation of claim 1.

9. The method according to claim 8, wherein the pediatric population is from 0 to 18 years of age.

10. The method according to claim 8, wherein the minitablet is administered to a patient in need thereof in an amount of not more than 0.5 mg/Kg of weight.

* * * * *